United States Patent
Austin et al.

(10) Patent No.: US 9,540,607 B2
(45) Date of Patent: Jan. 10, 2017

(54) FILL SYSTEM FOR PROVIDING UNIFORM CONCENTRATIONS AND VOLUMES AND METHODS THEREOF

(75) Inventors: Christopher D. Austin, Raleigh, NC (US); Patricia M. Whelton, Roxboro, NC (US); Sonya O. Meheux Sherwood, Durham, NC (US)

(73) Assignee: Cytonet, LLC, Durham, NC (US)

(*) Notice: Subject to any disclaimer, the term of this patent is extended or adjusted under 35 U.S.C. 154(b) by 0 days.

(21) Appl. No.: 13/401,259

(22) Filed: Feb. 21, 2012

(65) Prior Publication Data

US 2012/0305129 A1    Dec. 6, 2012

Related U.S. Application Data

(60) Provisional application No. 61/445,235, filed on Feb. 22, 2011.

(51) Int. Cl.
*B01L 3/02* (2006.01)
*C12M 1/26* (2006.01)
*F04B 43/12* (2006.01)
*A01N 1/02* (2006.01)

(52) U.S. Cl.
CPC ............ *C12M 33/00* (2013.01); *A01N 1/0236* (2013.01); *A01N 1/0263* (2013.01); *F04B 43/1292* (2013.01)

(58) Field of Classification Search
USPC .................................................. 422/521, 522
See application file for complete search history.

(56) References Cited

U.S. PATENT DOCUMENTS

| | | | | |
|---|---|---|---|---|
| 4,200,607 | A | * | 4/1980 | Suzuki ............................ 422/64 |
| 4,691,580 | A | * | 9/1987 | Fosslien ..................... 73/864.84 |
| 5,192,505 | A | * | 3/1993 | Sakagami ........................ 422/64 |
| 5,879,318 | A | | 3/1999 | Van der Heiden |
| 7,618,584 | B2 | | 11/2009 | Lampeter |
| 2003/0072679 | A1 | * | 4/2003 | Johnson et al. ................. 422/63 |
| 2003/0230488 | A1 | * | 12/2003 | Lee et al. ....................... 204/453 |
| 2006/0002824 | A1 | * | 1/2006 | Chang et al. .................. 422/100 |
| 2007/0105214 | A1 | * | 5/2007 | Micklash et al. .......... 435/306.1 |
| 2007/0259348 | A1 | * | 11/2007 | Phadke et al. ..................... 435/6 |
| 2008/0050275 | A1 | * | 2/2008 | Bischof et al. .................. 422/32 |
| 2009/0312523 | A1 | * | 12/2009 | Pellikka et al. ............... 530/345 |

OTHER PUBLICATIONS

International Search Report and Written Opinion received in PCT/US2012/025926, mailed Sep. 27, 2012.

* cited by examiner

*Primary Examiner* — Jill Warden
*Assistant Examiner* — Brittany Fisher
(74) *Attorney, Agent, or Firm* — Smith, Gambrell & Russell

(57) ABSTRACT

Disclosed herein are systems and methods for preparing a plurality of containers having a suspension of a solid wherein the concentrations of the solid in the plurality of containers are substantially similar or the same and the volumes of the suspension in the plurality of containers are substantially similar or the same.

6 Claims, 6 Drawing Sheets

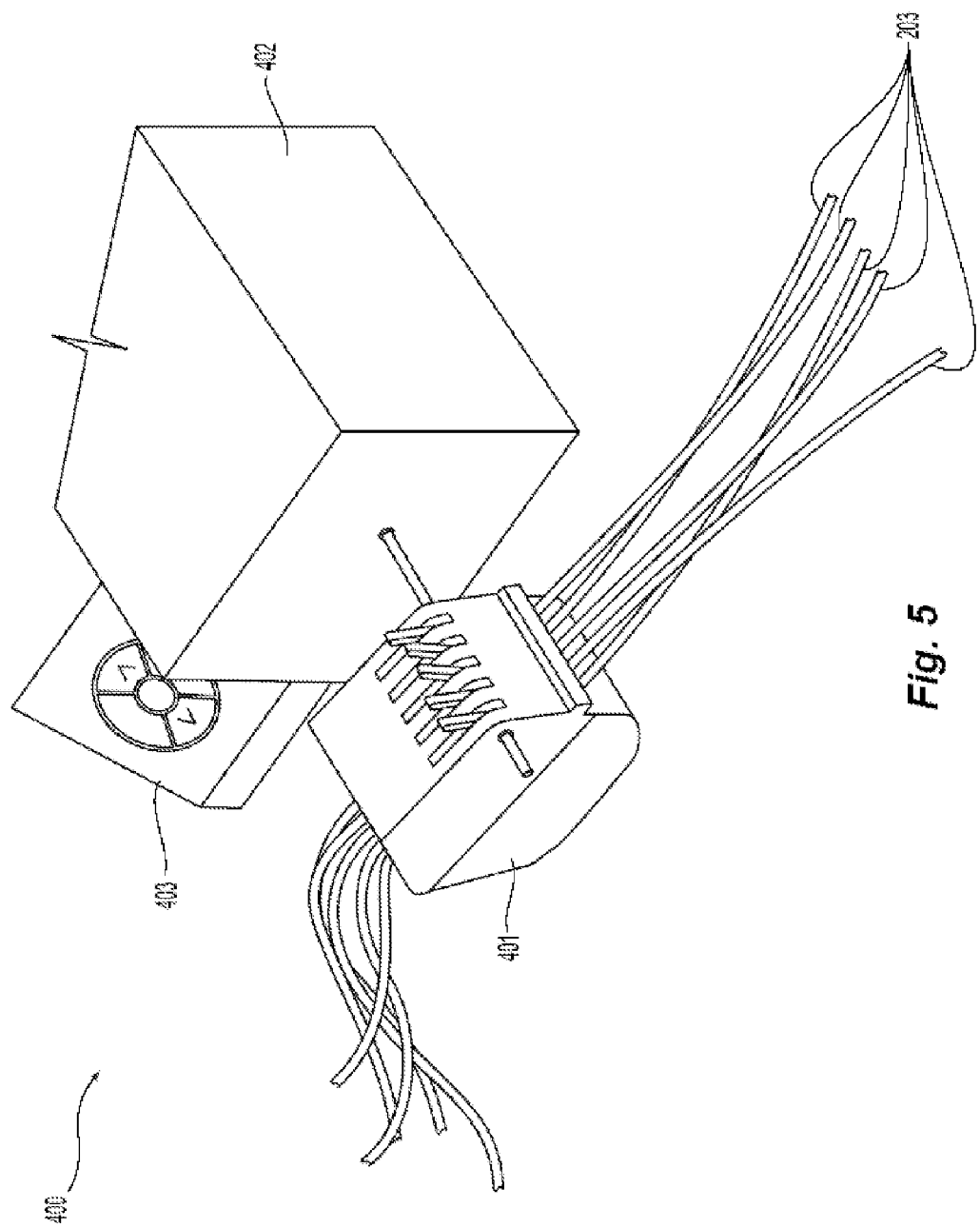

FILL SYSTEM FOR PROVIDING UNIFORM CONCENTRATIONS AND VOLUMES AND METHODS THEREOF

CROSS-REFERENCE TO RELATED APPLICATIONS

This application claims priority to U.S. Patent Application Ser. No. 61/445,235, filed Feb. 22, 2011, which is herein incorporated by reference in its entirety.

BACKGROUND OF THE INVENTION

1. Field of the Invention

The present invention generally relates to devices and methods for preparing, in a closed system, a cellular suspension for storage.

2. Description of the Related Art

With recent advances in cell transplantation, tissue engineering and genetic technologies, the living cell is becoming an important therapeutic tool in various medical treatments. The availability and efficacy of medical treatments involving the administration of living cells depends on successful preservation and storage of the living cells.

Cells can remain viable for months or years at cryogenic temperatures (e.g. temperatures below about 173 K). Such cryogenic temperatures are not generally lethal to cells. Instead, cell damage and cell death often occurs when the cells are prepared and cooled. Thus, storage of cells at cryogenic temperatures which are later suitable (viable) for use in medical treatments is possible where the cryogenic temperatures can be obtained without incurring fatal damage to the cells.

The two primary causes of fatal damage to cells during cooling are (1) the formation of ice crystals within the cells, and (2) the loss of water from the interior of the cell by osmosis. If freezing is carried out slowly, ice will tend to form outside the cell rather than inside. With further cooling, water from the interior of the cell will pass by osmosis through the cell membrane to add to the growing extracellular ice crystals. In leaving the cell, large and often fatal concentrations of solutes remain behind in the interior of the cell. Thus, rapid cooling is usually fatal to the cell due to intracellular ice formation; slow cooling is usually fatal due to high concentrations of solute inside the cell.

Various cyroprotectants are often used to avoid the formation of ice and/or delay the onset of ice formation to as low a temperature as possible. Such cryoprotectants known in the art are typically glycerol, dimethylsulfoxide (DMSO), ethylene glycol, propylene glycol, trimethylamine acetate, and other high molecular weight solutes capable of strongly hydrogen-bonding to water. Unfortunately, many cyroprotectants are toxic to cells under certain conditions, e.g. exposure to the cyroprotectant for a certain amount of time at a certain temperature. For example, DSMO is toxic to cells exposed thereto for periods of approximately 30 minutes or more at temperatures above 4° C.

Unfortunately, current devices and methods for the cryopreservation of cells do not allow fast and efficient cryopreservation of multiple cell preparations of uniform concentrations and volumes.

SUMMARY OF THE INVENTION

In some embodiments, the present invention is a fill system which comprises: a starting container; a system of fluid lines having a plurality of fluid lines; a plurality of containers; and a multichannel peristaltic pump having a pump head, wherein the starting container is connected to the system of fluid lines and each container of the plurality of containers is connected a fluid line of the plurality of fluid lines so as to form a closed system in which a fluid may flow from the starting container through the system of fluid lines to the plurality of containers; and the plurality fluid lines are engaged in the pump head such that operation of the multichannel peristaltic pump assists fluid flow through the system of fluid lines. In some embodiments, the closed system is a closed and sterile system. In some embodiments, the multichannel peristaltic pump may be operated in a forward direction or a reverse direction.

In some embodiments, the fill system further comprises a computer system having a computer program, and a controller which automatically, according to the computer program, operates the peristaltic pump, orientates and/or agitates the starting container, system of fluid lines, and/or the plurality of containers based on information received from one or more sensors.

In some embodiments, the present invention provides a closed and sterile system which comprises: a starting container; a system of fluid lines having a plurality of fluid lines; and a plurality of containers; wherein the starting container is connected to the system of fluid lines and each container of the plurality of containers is connected to a fluid line of the plurality of fluid lines so as to form a closed system in which a fluid may flow from the starting container through the system of fluid lines to the plurality of containers; and wherein the plurality fluid lines have fittings which can be used to secure the plurality of fluid lines in a pump head of a multichannel peristaltic pump.

In some embodiments, the closed system of the present invention comprises a starting material, an additive, or both. In some embodiments, the starting container comprises a starting material which contains a biomolecule, preferably liver cells, to be distributed as a suspension in the plurality of containers. In some embodiments, the closed system comprises of a cyroprotectant to be mixed with a starting material or added to the plurality of containers. In some embodiments, the components forming the closed system are made of biocompatible materials. In some embodiments, the plurality of fluid lines are made of platinum cured silicone. In some embodiments, the system of the invention further comprises at least one syringe. In some embodiments, the system of the invention further comprises a second system of fluid lines having a second plurality of fluid lines which may be engaged in a second pump head of a second peristaltic pump.

In some environments, the present invention provides a method of preparing a plurality of containers having a suspension of a solid wherein the concentrations of the solid in the plurality of containers are substantially similar or the same and the volumes of the suspension in the plurality of containers are substantially similar or the same, which comprises: obtaining a closed and sterile system as disclosed herein, providing a starting material having the solid therein in the starting container, engaging the plurality of fluid lines in a pump head of a peristaltic pump, operating the peristaltic pump in a forward direction so as to cause the starting material to flow from the starting container to the plurality of containers, and optionally adding an additive to the starting material. In some embodiments, the method further comprises removing an excess fluid from the plurality of containers by operating the peristaltic pump in a reverse direction so as to cause the excess fluid to flow from the plurality of containers towards the starting container. In some embodiments, the method further comprises sealing off and detaching the plurality of containers.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 5 schematically shows a peristaltic pump according to the present invention.

DETAILED DESCRIPTION OF THE INVENTION

Figure 1:
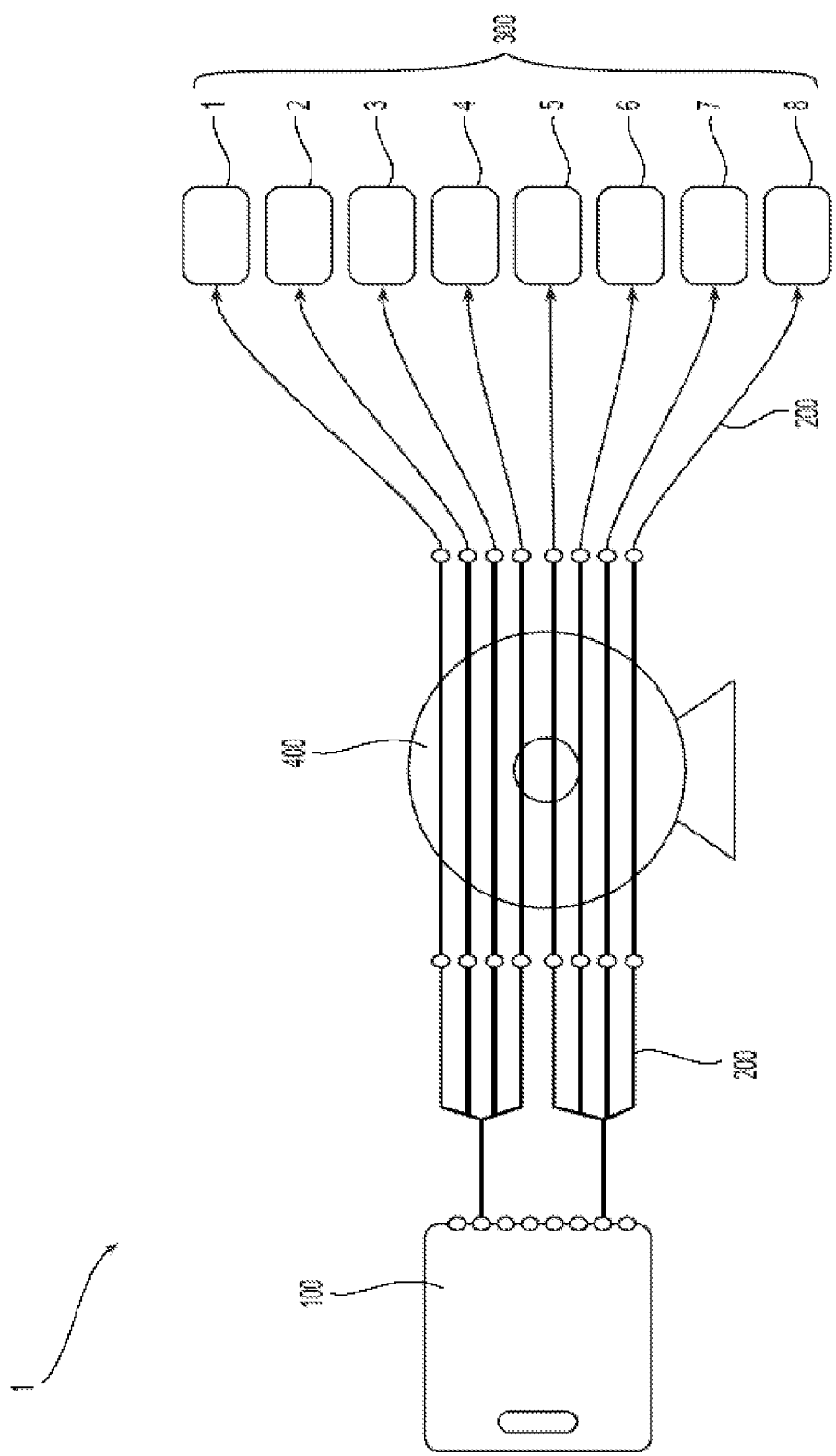
FIG. 1 schematically shows an exemplary fill system according to the present invention.

The present invention provides devices, systems and methods for preparing a plurality of containers having a suspension of a solid, wherein the concentrations are uniform concentrations, i.e. the concentrations of the solid in the plurality of containers are substantially similar or the same, and the volumes of the suspension are uniform volumes, i.e. the volumes of the suspension in the containers are substantially similar or the same. As used herein, a "substantially similar" concentration means that the concentrations of the solid in the containers differ by not more than 10%, preferably not more than 5%, more preferably not more than 2.5%, most preferably not more than 1%. As used herein, a "substantially similar" volume means that the volumes of the suspension in the containers differ by not more than 10%, preferably not more than 5%, more preferably not more than 2.5%, most preferably not more than 1%. In some embodiments, the solid is a "biomolecule" such as a cell, protein, polysaccharide, lipid, nucleic acid molecule, and the like. The cells may be of any origin, e.g. bacterial, mammalian, insect, animal, human, etc., and may be recombinant, cultured, or isolated from a natural source. In some embodiments, the cells are liver cells, stems cells, erythrocytes, leukocytes, and the like. In some embodiments, the suspension comprises more than one type of solid, e.g. liver cells and stem cells.

In some embodiments, the components of the devices and systems of the present invention are provided as a closed system. As used herein, a "closed system" refers to the internal cavity of a structure that is selectively isolated from the external environment by one or more walls of the components forming the structure. As used herein, "selectively isolated" means that a desired substance may be actively introduced into the internal cavity and/or actively removed from the internal cavity without exposing the internal cavity to substances other than the desired substance. A closed system may be a closed and sterile system. As used herein, "a closed and sterile system" refers to a closed system that has been sterilized and/or a closed system that is substantially free of one or more biological contaminants. As used herein, a closed system that is "substantially free of biological contaminants" may contain one or more biological contaminants in amounts that do not generally result in deleterious and injurious effects. In some embodiments, one or more of the components of the devices and systems of the present invention are provided as individual components, each of which are a closed system, which may then be joined to each other to form a closed system. In these embodiments, the components are preferably joined using methods and devices known in the art which prevent the introduction of contaminant therein. In some embodiments, a joint between components is formed using methods and devices known in the art which result in the joint being hermetically sealed. In some embodiments, some or all of the joints are hermetically sealed.

According to the present invention, a multichannel peristaltic pump is used to dispense a solid of a starting material from a starting container through a plurality of fluid lines from a pump head into a plurality of containers. Multichannel peristaltic pumps such as those commercially available from: Cole-Parmer, Vernon Hills, Ill.; Ismatec (e.g. 16 channel roller pump), Wertheim-Mondfeld Germany; Watson Marlow, Inc., Wilmington, Mass.; and the like may be employed in accordance with the invention as disclosed herein. The pump head may be a stackable or a cartridge pump head known in the art.

In some embodiments, a starting material containing the solid is provided in one or more starting containers. As used herein, a "container" refers to a structure in which a substance, such as a fluid and/or solid, may be contained therein for a desired period of time. In some embodiments, one or more containers of the present invention have flexible walls. In some embodiments, one or more containers are semi-rigid and/or rigid. The containers of the present invention may be of any shape and size. In some embodiments, the shape and size of a given container is suitable for a given action to be performed on the container. Those skilled in the art may readily select shapes and sizes of containers that are suitable for a given action or actions to be performed on the container. Examples of commercially available containers include: the Fenwal Collection Containers and BLOOD-PACK® bags (Fenwal, Inc., Lake Zurich, Ill.); CRYO-CYTE® bags (Baxter, Deerfield, Ill.); PEDI-PAK® Transfer Packs (Genesis BPS, Hackensack, N.J.); MINI-PLASCO® containers (B. Braun, Melsungen, Germany); and the like.

In some embodiments, the starting material may be the suspension itself, i.e. the suspension containing the solid that is dispensed into the plurality of containers without any prior processing, e.g. mixed with one or more additional ingredients. In some embodiments, the starting material containing the solid may be from a single source or a plurality of sources (i.e. a pooled mixture). In some embodiments, the solid in the starting material is first concentrated or diluted to a desired concentration. In some embodiments, one or more additives are added to the starting material and, in these embodiments, the mixture is a suspension containing the solid. In some embodiments, one or more additives are added before, during, and/or after the starting material is added to the plurality of containers. Additives include any compound or composition desired to be included in the suspension for any given purpose, e.g. further processing or storing of the suspension. The additive may be a pre-made composition of a plurality of ingredients or a single ingredient. For example, the additive may be a freezing medium known in the art and/or commercially available in the art or the additive may be a single ingredient such as a cyroprotectant, e.g. ethylene glycol, propylene glycol, glycerol, dimethyl sulfoxide (DSMO), sucrose, etc.

As used herein, a "fluid line" refers to a structure through which a fluid may flow. Although a fluid line is capable of containing a substance therein, such that a fluid line is a container, as defined herein, a "fluid line" refers to a structure through which a fluid flows that has a cross-sectional volume that is smaller than both the cross-sectional volume of the structure from which the fluid originates and the cross-sectional volume of the structure to which the fluid flows. In other words, a cross-sectional volume of a container is larger than that of a fluid line connected thereto. One or more fluid lines in the devices of the present invention may be flexible and/or semi-rigid. The fluid lines of the present invention may have one or more desired cross-sectional shapes. In some embodiments, one or more fluid lines of the devices of the present invention have a round cross-sectional shape. In some preferred embodiments, one or more fluid lines are tubular in shape. In some preferred embodiments, one or more fluid lines are flexible tubing made of a biocompatible material. A fluid line, according to the present invention, may be an integral part of one or more containers or a separate and distinct component that is joined to a container of the device. In some embodiments, one or more fluid lines of the present invention are made of platinum cured silicon.

One or more fluid lines from a starting container deliver the starting material to the pump head of the multichannel peristaltic pump. Where a plurality of fluid lines are employed, the plurality of fluid lines may be provided in a housing. In some embodiments, a fluid line from the starting container branches in to multiple fluid lines which then connect to the pump head. In some embodiments, fluid lines from two or more starting containers deliver the starting material to the pump head.

In some embodiments, the peristaltic pump includes rollers that roll across the fluid lines and thereby limit distortion of the tubing and increase flow accuracy. In some embodiments, the flow drive mechanism of the peristaltic pump is reversible such that fluid flow to and from the pump head may be reversed. For example, instead of pumping fluid to the plurality of containers, the flow drive mechanism may be reversed such that fluid from the plurality of containers flows toward the pump head.

In some embodiments, a fluid line may be connected to a container and/or to more fluid lines. The connection may be a direct connection, e.g. one component directly connected to another component at a joint, or an indirect connection, e.g. a fluid line connector, between the components. As used herein, a "fluid line connector" is a structure that provides a sealed, preferably a hermetically sealed, connection between the connected components. A fluid line connector of the present invention may be a bidirectional connector, i.e. a connector that allows fluidic communication from a first component on a first side of the connector to a second component on a second side of the connector and vice versa, or a unidirectional connector, i.e. a connector that allows fluidic communication in only one direction, e.g. from a first side of the connector to a second side of the connector. In some embodiments, at least one fluid line connector may be a one-to-one connector, i.e. a fluid line connector that allows only two components to be directly connected to each other. In some embodiments, at least one fluid line connector may be a multi-connector, i.e. a fluid line connector which contains a plurality of connection points capable of connecting a plurality of components (e.g. one or more fluid lines and/or one or more containers), wherein one or more components of the plurality of fluid lines may or may not be connected to one or more additional fluid lines. The connectors may employ a wide variety of securing mechanisms, including, but not limited to luer lock mechanisms, snap-fit mechanisms, threaded male/females assemblies, and the like. In some embodiments, the fluid line connector may be a spike connector such a Benjamix spike connector by B. Braun, Melsungen, Germany. Examples of commercially available fluid lines and fluid line connectors include DISCOFIX® three-way stopcock valves (B. Braun, Melsungen, Germany); plasma transfer sets (Baxter, Deerfield, Ill.); Y-connectors with open injection sites (Genesis BPS, Hackensack, N.J.); and the like.

According to the present invention, one or more of the fluid lines may contain a fluid flow regulator. In some embodiments, a fluid line connector may also be a fluid flow regulator. As used herein, a "fluid flow regulator" is a structure capable of regulating the flow of a fluid. A fluid flow regulator may be capable of either allowing unrestricted fluid flow or completely preventing a fluid from flowing from one side of the fluid flow regulator to the other side of the fluid flow regulator. In some embodiments, a fluid flow regulator may restrict some, but not all of the fluid flow. In some embodiments, where the fluid flow regulator restricts some, but not all of the fluid flow, the fluid flow regulator may also be capable of allowing unrestricted fluid flow and/or completely preventing a fluid from flowing from one side of the fluid flow regulator to the other side of the fluid flow regulator.

A fluid flow regulator may be positioned within the internal cavity of the fluid line and may be provided as an integral part of the interior walls of the fluid line or as a separate and distinct component that is joined to the interior walls of the fluid line. Alternatively, a fluid flow regulator may be externally positioned along the fluid line and may or may not be removably attached to the exterior walls of the fluid line. A fluid flow regulator of the present invention may be a bidirectional regulator, i.e. a regulator that regulates fluid flow from a first component on a first side of the regulator to a second component on a second side of the regulator and vice versa, or a unidirectional regulator, i.e. a regulator that regulates fluid flow in only one direction, e.g. from a first side of the regulator to a second side of the regulator. A fluid flow regulator may be of any desired shape or size so long as it performs its desired function. Such shapes and sizes for a desired flow of fluid, or lack thereof, may be readily determined by those skilled in the art. In some embodiments, multiple fluid flow regulators may be placed on or in a given fluid line. In some embodiments, two fluid flow regulators are provided as a pair of regulators along a fluid line. The fluid flow regulators belonging to a pair of regulators may be of the same or different size, shape, material and/or type. Additionally, the pair of regulators may be positioned within the internal cavity of the fluid line or externally positioned. Alternatively, one fluid flow regulator may be positioned within the internal cavity of the fluid line and the other fluid flow regulator may be externally positioned along the fluid line.

A fluid flow regulator, alone or in pairs, may be used to isolate and/or separate a component, such as a container, from a closed system (a) without leaking or exposing the contents of the component to the external environment, and (b) without exposing the remaining closed system to the external environment by "sealing off" the part of the fluid line between the pair of fluid flow regulators by using the fluid flow regulators to prevent any fluid flow there between and then severing the fluid line between the pair of fluid flow regulators. Alternatively, one or more parts of the fluid line connecting the component to be separated and/or removed from a closed system may be permanently sealed, thereby "isolating" the component from the closed system, and optionally, the component may be "separated" from the closed system by severing the fluid line between two permanent seals or somewhere in the middle of a single permanent seal using methods and devices known in the art. In some embodiments, the formation of a permanent seal results in both isolation and separation of the component. For example, heat may be applied to a part of the fluid line such that the fluid line becomes heat sealed while a portion is melted away, thereby severing the fluid line while permanently sealing the ends of the fluid line that become disconnected. Such methods may be used upon completion of the distribution process to store the storage container. Examples of commercially available fluid flow regulators include slide clamps (Fenwal, Inc., Lake Zurich, Ill.); pinch clamps (Halkey-Roberts Corp., Saint Petersburg, Fla.); in-line stopcock valves; and the like.

In some embodiments, at least one access port that allows access into and/or out of one or more components, e.g. containers or fluid lines, is provided. In some embodiments, at least one port may be a one-to-one port, i.e. a port that allows only a single access point between, into and/or out of a given component. In some embodiments, at least one port may be a multi-port, i.e. a port which contains a plurality of access points into and/or out of a given component. In some embodiments, at least one inlet port and at least one outlet port are provided. As used herein, an "inlet port" is a structure through which a desired substance may be actively introduced into a closed system without exposing the closed system to substances other than the desired substance. As used herein, an "outlet port" is a structure through which a desired substance may be actively distributed from one device to another or removed from a closed system without exposing the closed system to substances other than the desired substance.

A port of the present invention may be a bidirectional port, i.e. a port that allows both access into and out of a closed system, or a unidirectional port, i.e. a port that allows access in only one direction. A port may be a multi-use port, i.e. a structure which allows repeated access into a closed system and/or repeated access out of a closed system. Alternatively, a port may be a single-use port, i.e. a structure that can be used only once to allow one-time access into and/or one-time access out of a closed system. For example, a single-use port may be permanently sealed closed by its use or after its use. A port, according to the present invention, may be provided as an integral part of a container or a fluid line. Alternatively, a port may be a separate and distinct component that is connected directly to a container or a fluid line at a joint or indirectly connected to the container or the fluid line via a fluid line connector. In some embodiments, a port may also be a fluid line connector, i.e. may be used as either a port or a fluid line connector which connects an additional component thereto. Examples of commercially available ports include: sealed luer locks (Halkey-Roberts Corp., St. Petersburg, Fla.); resealing rubber septums; PEDI-PAK® Pedi-Syringe Filter™ devices (Genesis BPS, Hackensack, N.J.); and the like. In some embodiments, the port may be a sterile port that allows aseptic fluid transfer. In some embodiments, the port is kept sterile until a fluid line connecter is attached thereto. In some embodiments, the port is a spike port and the fluid line connector is a spike connector.

In some embodiments, the devices and systems of the present invention may contain one or more syringes. The syringes may be used to remove a fluid, e.g. air or an aliquot of the suspension, from one or more components. The syringes may also be used to displace a fluid within one or more components.

The components (i.e. containers, fluid lines, fluid line connectors, fluid flow regulators, ports, and syringes) of the devices of the present invention may be made of plastics, glass, metals, and the like, and combinations thereof. In some embodiments, some or all of the components of the devices of the present invention are made of one or more materials which are compatible with the given suspension. In embodiments where the solid is a biomolecule, the components are preferably made of materials that are biocompatible with a given biomolecule, e.g. cell suspension and reagents used to process the given cell suspension, e.g. additives. As used herein, a thing, such as a composition or a material, or a process conducted on the thing is referred to being "biocompatible" where the thing or the process does not have a toxic or injurious effect on a given biomaterial to be processed, reagents that will be used to process the given biomaterial, the resultant processed biomaterial, the particular subject to be treated, under the conditions of exposure thereto, and the actions to be performed thereon. In some embodiments, the methods and devices of the present invention and/or the methods and devices that are used in accordance with the present invention are biocompatible. A "biocompatible material" is a material that does not have a toxic or injurious effect on a given biomaterial, reagents that will be used to process the given biomaterial, the resultant processed biomaterial, the particular subject to be treated, under the conditions of exposure thereto, and the actions to be performed thereon. Such biomaterials may or may not meet one or more of the various biocompatibility standards as required by the U.S. Food and Drug Administration.

Exemplary Configurations

FIG. 1 schematically shows a fill system 1 according to the present invention which may be used for preparing a plurality of containers having uniform concentrations and volumes of a suspension, such as a cell suspension. As shown, the fill system 1 comprises a starting container 100, a system of fluid lines 200 (including fluid line connectors), a plurality of containers 300, and a peristaltic pump 400. The fill system 1 is a closed system.

Figure 2A:
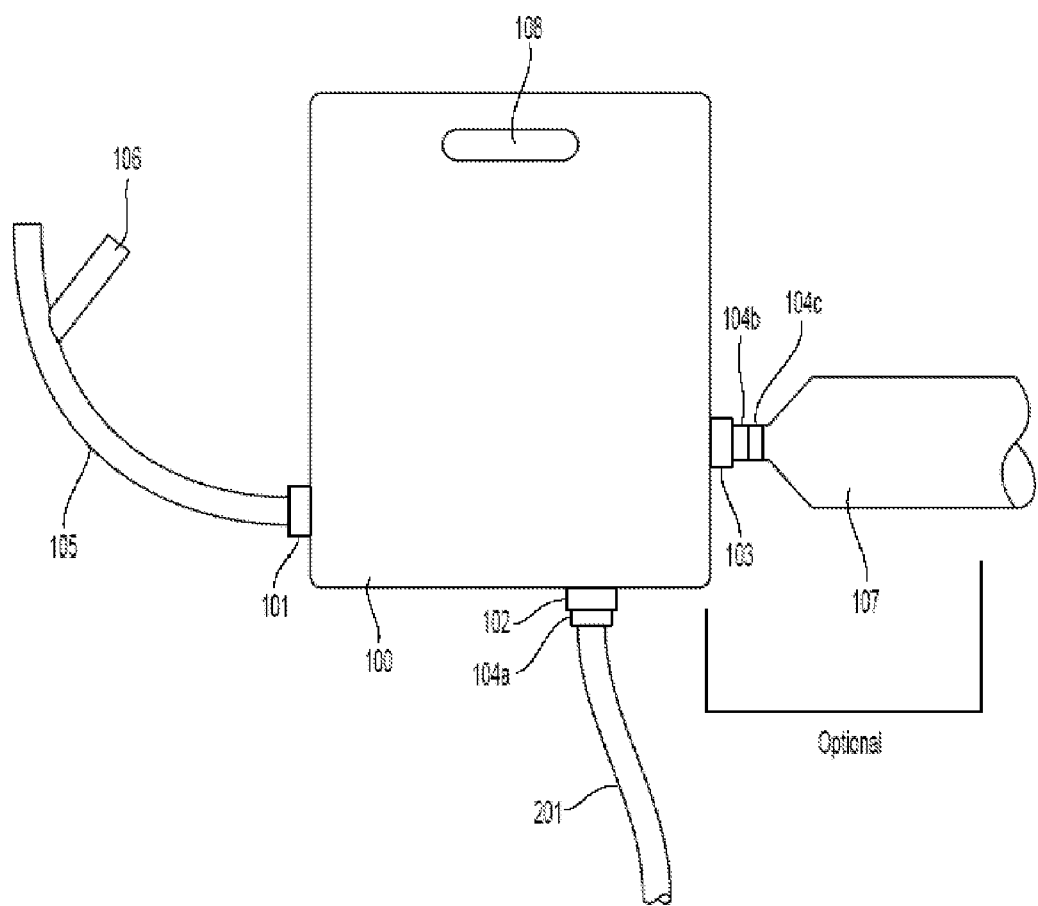
FIGS. 2A and 2B schematically show exemplary starting containers according to the present invention.

FIG. 2A, schematically shows a starting container 100 according to the present invention. The starting container 100 may be of any desired shape or size or volume. In some embodiments, the starting container has a total volume that is large enough to allow effective mixing of a desired volume of a starting material. As shown in FIG. 2A, the starting container 100 includes an inlet port 101 and an outlet port 102. Preferably, the inlet port 101 and the outlet port 102 are configured to allow the aseptic transfer of a fluid into and out of the starting container 100. Also shown is a bidirectional port 103. The bidirectional port 103 allows the addition of a fluid to the starting container 100 and the removal of a fluid from the starting container 100. The ports 101, 102, and 103 allow the addition or removal of a material from the starting container, e.g. the addition of a starting material from one or more sources and additives into the starting container and/or the removal of air and aliquots of the suspension from the starting container. In some embodiments, the starting container 100 may have a plurality of inlet ports 101. In some embodiments, the starting container 100 may have no inlet port 101. In such embodiments, the starting material may already be provided in the starting container 100. For example, the starting material is prepackaged in the starting container and then fluid lines are connected to the outlet port 102.

As shown in FIG. 2A, ports 102 and 103 have fluid line connectors 104a and 104b (such as spiked connectors (with a luer on the outer end) that connects to a stopcock valve), respectively, attached thereto and fluid line connector 104b has a fluid flow regulator 104c. In some embodiments, one or more of the fluid line connectors may also be a fluid flow regulator. In some embodiments, the ports may have a section of a fluid line connected thereto with the other end of the section of the fluid line being hermetically sealed. FIG. 2A shows port 101 having a section of a fluid line 105 connected thereto which is hermetically sealed at its free end. In some embodiments, such sections of fluid lines may be joined with another fluid line under conditions which do not introduce a contaminant therein in order to add additional components or materials to the starting container 100. In some embodiments, a part of a section of a fluid line, e.g. fluid line 105, may be removed in order to test or analyze the substance therein. In some embodiments, the fluid lines may also contain ports for obtaining a sample of the substance therein. FIG. 2A shows the section of a fluid line 105 having a port 106.

As shown in FIG. 2A, a syringe 107 is connected to the bidirectional port 103 with the fluid line connector 104b and the fluid flow regulator 104c. The syringe 107 may be used to dispense a substance such as an additive into the starting container. The syringe 107 may be used to remove an aliquot of the suspension from the starting container. In some embodiments, the syringe is used to add or remove air from the closed system. In some embodiments, the fluid line connector 104b (which connects the syringe 107 to the bidirectional port 103) can be a fluid flow regulator, such as an in-line stopcock valve. In some embodiments, the fluid line connector 104b can be a spike connector. In some embodiments, the fluid flow regulator 104c is absent. In some embodiments, the syringe 107 may be connected directly to the port 103.

While the embodiment set forth in FIG. 2A makes a distinction between the inlet port 101, the outlet port 102, and the bidirectional port 103, in other embodiments, these ports may or may not be bidirectional. Similarly, one or more of these ports may be integral with the starting container rather than being separate components that are hermetically joined to the starting container.

As shown in FIG. 2A, the starting container 100 may also include a securing component 108, such as an aperture or a hook, which allows the starting container 100 to be securely oriented in a desired manner, e.g. oriented such that that the outlet port 102 is at the top or the bottom of the starting container 100. The securing component 108 may be configured to attach to a physical structure such as a hook such that the desired orientation of the starting container is fixed by being attached to the physical structure. The securing component 108 of the collection container 100 is not limited to just an aperture. The securing component 108 may be anything, e.g. a clip, a hook, an adhesive, etc., that allows the starting container to be affixed to a desired physical structure.

Figure 2B:
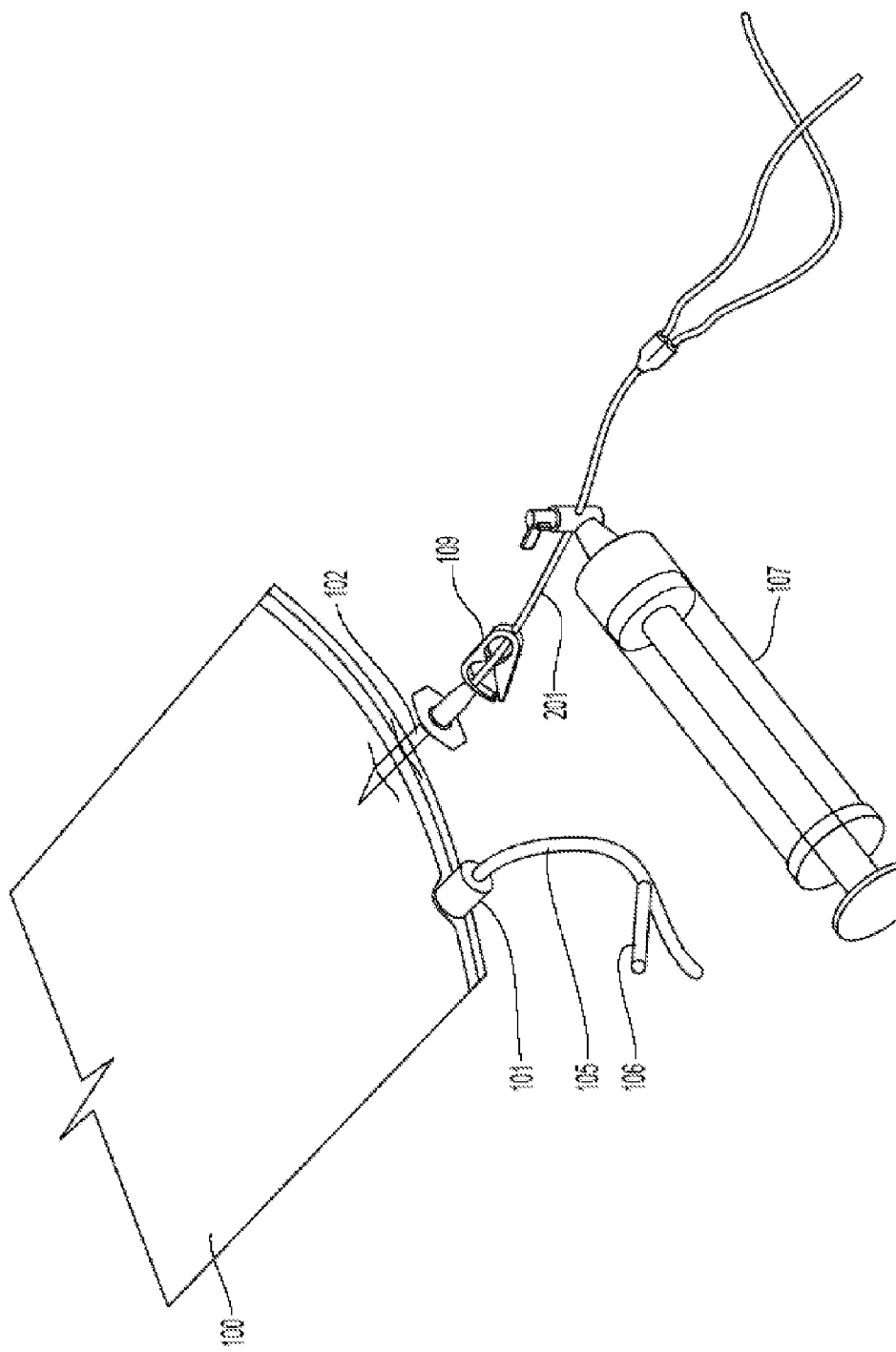

FIG. 2B schematically shows an alternative embodiment of a starting container according to the present invention. As shown in FIG. 2B, the syringe 107 is connected to the fluid line 201 connected to port 102. The fluid flow regulator 109 is optional.

Figure 3:
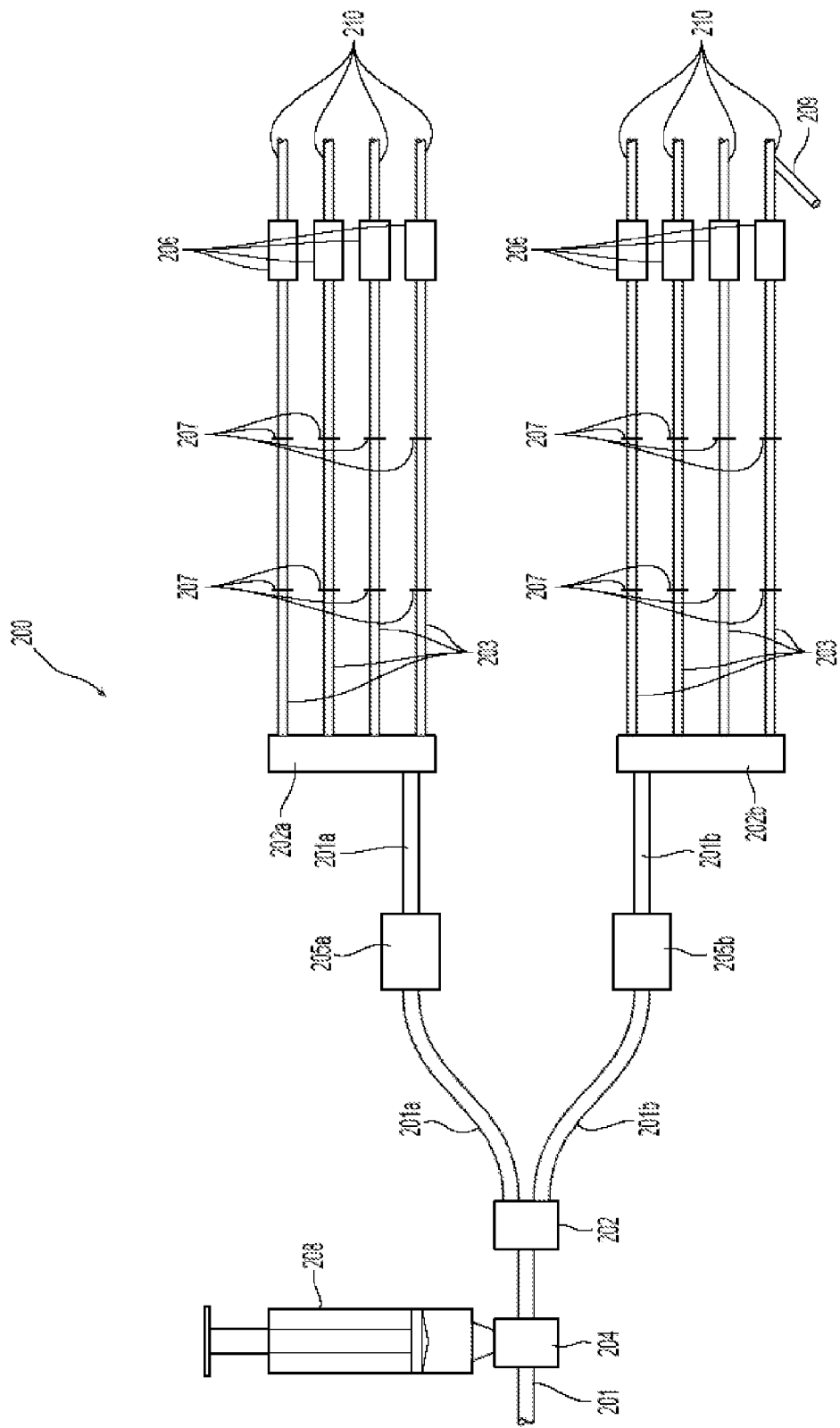
FIG. 3 schematically shows a system of fluid lines according to the present invention.

FIG. 3 schematically shows a system of fluid lines 200 which connect the starting container to the plurality of containers. As shown in FIG. 3, the system of fluid lines 200 comprises a plurality of fluid lines 201, 201a, 201b, 203, fluid flow connectors 202, 205a, 205b, fluid flow regulators 204, 206, fittings 207, syringe 208 and port 209. Port 209 can be used to remove an aliquot for testing and/or add an additive thereto. As shown in FIG. 3, fluid line 201 is connected to a multi-connector 204 which connects the fluid line 201 to fluid lines 201a and 201b. Fluid line 201a is connected to multi-connector 202a and fluid line 201b is connected to multi-connector 202b. Multi-connectors 202a and 202b connect fluid lines 201a and 201b, respectively, to a plurality of fluid lines 203. While a variety of different fluid lines may be used, in some embodiments, the cross-sectional shape and length of each fluid line 203 is substantially similar or the same. In some embodiments, each segment of fluid line (e.g. 201a, 203, etc.) may be made of the same or different material as fluid line 201. In embodiments where segments of fluid lines are connected to form the system of fluid lines 200, each segment may be directly or indirectly connected a given component. For example, fluid line 203 may be directly connected to multi-connector 202a or it may be indirectly connected thereto by way of a fluid line connector such as a luer.

In some embodiments, the fluid flow regulator 204 is an in-line fluid flow regulator and fluid line 201 is one piece. In some embodiments, fluid line 201 is two pieces which are connected by the fluid flow regulator 204. In some embodiments, fluid flow regulator 204 and syringe 208 are absent. Similarly, in some embodiments, fluid flow regulator 205a (and/or 205b) is in-line fluid flow regulator and fluid line 201a (and/or 201b) is one piece. In some embodiments, fluid line 201a (and/or 201b) is two pieces which are connected by the fluid flow regulator 205a (and/or 205b). In some embodiments, fluid flow regulator 205a (and/or 205b) is absent.

The multi-connectors 202, 202a, and 202b can connect one fluid line to any desired number of fluid lines. For example, multi-connector 202a may connect fluid line 201a to 2 fluid lines or 10 fluid lines. Alternatively, one or more of the multi-connectors 202, 202a, and 202b may be a one-to-one fluid line connector. In other words, any combination of any number of fluid lines and any number of multi-connectors may be employed so long as the number of fluid lines forming the plurality of fluid lines 203 is at least the same number of the containers to be filled with the suspension. In embodiments where the number of fluid lines 203 is greater than the number of containers to be filled with the suspension, the flow of fluid in the extra fluid lines may be prevented by, for example, a fluid flow regulator. While the embodiment exemplified in FIG. 3 employs a combination of fluid lines and multi-connectors to form a branched system of fluid lines, a single fluid line which branches into a plurality of fluid lines may be used instead of multi-connectors.

Fluid flow regulators 205a, 205b and 206 may be used to control the flow of fluid. For example, where flow to multi-connector 202b is not desired, fluid flow regulator 205b may be engaged. Fluid lines 201 are the fluid lines that lead to the plurality of containers 300. As noted above, if the number of containers to be filled is less than the number of fluid lines 203, one or more fluid flow regulators 206 may be engaged to stop fluid flow in the extra fluid lines. The fluid flow regulators 204, 205a, 205b and 206 may be engaged to prevent the flow of fluid from the containers. Alternatively, when desired the fluid flow regulators 204, 205a, 205b and 206 may be engaged to allow the flow of fluid from the containers. For example, air which accumulates in the containers may be caused to flow from the containers toward the starting container. The fluid flow regulator 204, which is preferably an in-line fluid flow regulator such as a stopcock valve, may be engaged such that the air may be removed from the fluid line 201 using the syringe 208. Fluid flow regulators 205a, 205b and 206 may be pinch clamps, roller clamps, and the like, or a combination thereof. Although all the fluid flow regulators of a device according to the present invention need not be the same, where different types of fluid flow regulators are used, it is preferred that the fluid flow regulators are capable of regulating fluid flow such that the fluid flow in fluid lines 203 are substantially similar or the same.

The fittings 207 are used to attach the plurality of fluid lines 203 to the pump head of the peristaltic pump. The fittings 207 may be attached to the plurality of fluid lines 203 either upstream or downstream of fluid flow regulators 206. Although one or more fluid lines 203 may be split into additional fluid lines downstream of the fittings 207, such configurations are not preferred as the fluid flow through the fluid lines to the containers will not likely be as consistent as fluid flow through the fluid lines where each fluid line is equally acted upon by the pump head of the peristaltic pump.

In some embodiments, the syringe 208 may be used to push fluid in the fluid lines into the containers. For example, when there is no more fluid on the starting container side of the pump head, to push the fluid on the container side of the pump head, a fluid in the syringe 208 may be used to push the fluid on the container side of the pump head into the containers. In some embodiments, the syringe 208 may be used to remove a sample of the fluid in the fluid lines for testing. In some embodiments, the syringe 208 may be used to move a gas, such as air, in and out of the fluid lines.

Figure 4:
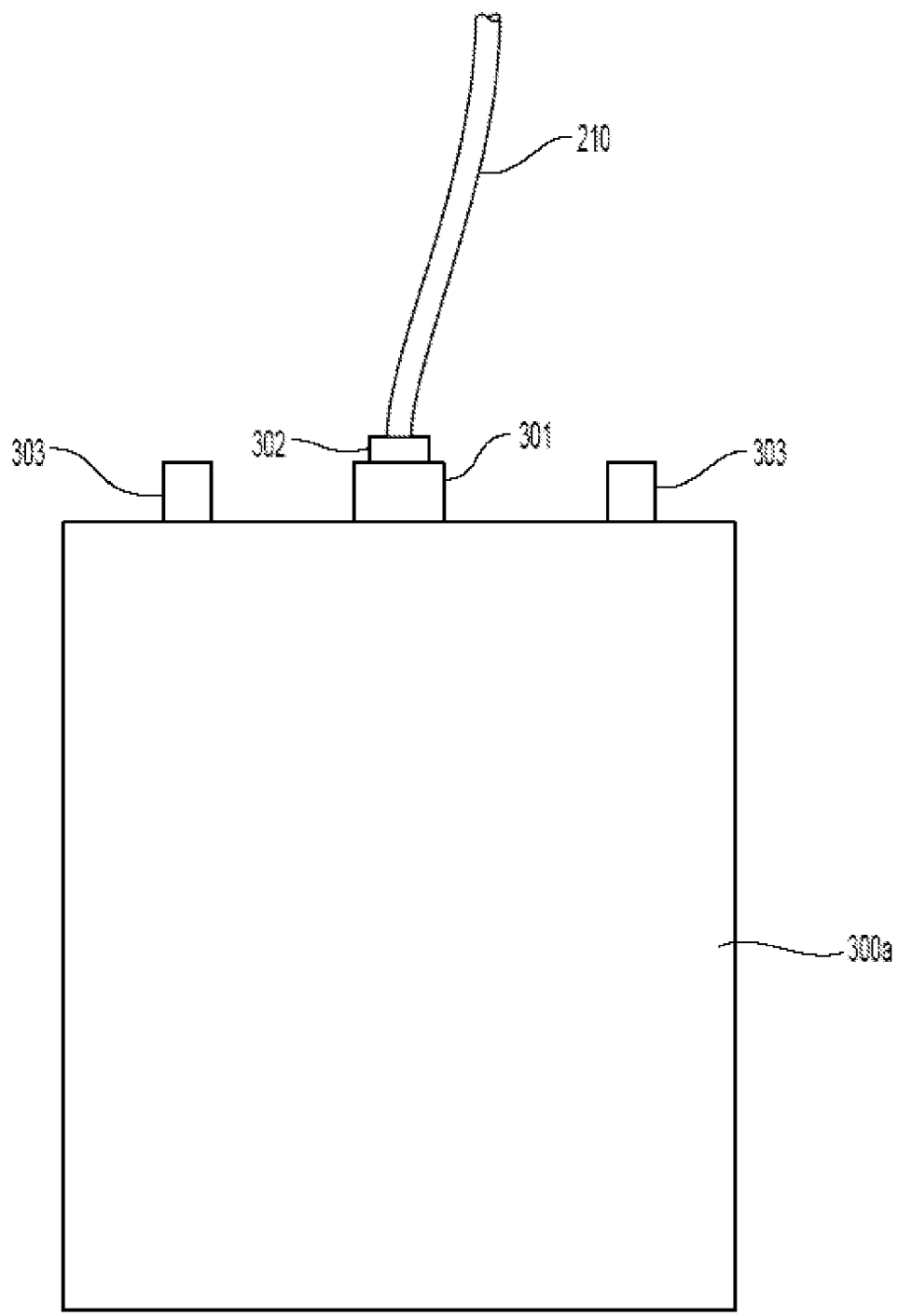
FIG. 4 schematically shows a container of the plurality of containers according to the present invention.

FIG. 4 schematically shows one of the containers in the plurality of containers 300. As shown in FIG. 3, a container 300a contains a port 301 to which a fluid line may be connected. The port 301 may be an integral part of the container 300a. The port 301 may or may not have a fluid line connector 302 connected thereto. The container 300a may have one or more additional ports 303. A port 303 may be used to remove the suspension from the container 300a. The containers belonging to the plurality of containers 300a may be of any shape or size. In some embodiments, the containers belonging to the plurality of containers 300a have the same shape and size. In some embodiments, the sum of the volume of the containers is at least the same as the total volume of the suspension. In some embodiments, the container 300a is composed of one or more biocompatible materials known in the art. In some embodiments, the containers 300 may withstand temperatures of about −180° C. without breaking or cracking.

In some embodiments, the port 301 and/or the fluid line connector 302 may be permanently sealed after the container 300a has been filled with the suspension. In some embodiments, a portion of a fluid line connected to the port 301 or the fluid line connector 302 may be left attached thereto and permanently sealed after the container 300a has been filled with the suspension. In some embodiments, the container 300a may include a secondary chamber which is or can be isolated away from its primary chamber. The container 300a may further include one or more ports for accessing the suspension therein in order to, for example, test the suspension at a later date. In some embodiments, the ports 301 and 302 are multi-use ports. In some embodiments, the container 300a may lack a port 303 and instead, port 301 may be used to both add the suspension into the container 300a and to remove the suspension from the container 300a.

FIG. 5 schematically shows a peristaltic pump 400 according to the present invention where the pump head 401 is a multi-channel cassette pump head having a plurality of fluid lines engaged therein. According to the present invention, the peristaltic pump 400 comprises a pump head 401, an engine driven rotor 402, and rollers. In some embodiments, the rollers of the engine driven rotor 402 can be rotated in a forward direction and in a reverse direction. The rollers simultaneously push and pull fluid in a fluid line engaged in the pump head 401 toward the containers when the engine driven rotor 402 is operated in the forward direction or toward the starting container when the engine driven rotor 402 is operated in the reverse position. In particular, when a roller of the engine driven rotor 402 engages the surface of a fluid line, the fluid is compressed to the point of closing the portion that is in contact with the roller, thereby forcing the fluid in front of the closed portion forward while sucking the fluid behind the closed portion forward. In some embodiments, the engagement of the fluid lines in the pump head 401 does not breach the closed system. The engine driven rotor may be controlled by a control system. The control system can include a user interface 403 that allows for the operation of the peristaltic pump 400 and the input of certain parameters, such as direction, rpms, operation time, and the like. The control system may also employ a sensor for automatic functions such as determining the presence of the suspension in the fluid lines engaged in the pump head 401 and modifying its parameters of operation accordingly. For example, the sensor can alert the control system when the suspension is not contained in the fluid lines engaged in the pump head 401 and then the control system may either stop the pumping operation or reverse the rotation of the engine driven rotor 402 to move a fluid from the containers toward the pump head 401.

In some embodiments, the starting container and/or the plurality of containers are provided on (or in) one or more holders which are capable of adjusting the relative elevations of the containers and/or agitate the containers. In some preferred embodiments, the components on the right side of the pump head have a maximum volume capacity that is the same as or substantially similar to the components on the left side of the pump head. For example, when the maximum volume capacities are the same, the left side is filled to its maximum capacity with a fluid, and the right side is completely void, the total volume of the fluid can be moved into and completely contained by the components on the right side. In some preferred embodiments, the maximum volume capacity of the starting container(s) is the same as or substantially similar to the total sum of that of the plurality of containers. For example, in some embodiments, the starting container has a 1 L capacity and the plurality of containers consists of 10 containers, each of which is capable of containing 100 mL.

Exemplary Assembly

Devices and fill systems according to the present invention may be assembled and operated using methods known in the art. In preferred embodiments, the fill systems according to the present invention are closed and sterile systems. Such closed and sterile systems may be made by assembling all the individual components in a sterile environment, such as a biological safety cabinet (BSC). Alternatively, portions of a fill system, e.g. starting container, system of fluid lines, and a plurality of containers, may be assembled as closed and sterile systems in a sterile environment and then joined together, thereby forming one closed and sterile system that is substantially free of biological contaminants, using methods known in the art. In these embodiments, the closed and sterile systems may be joined together while in a sterile environment or under conditions which may not be sterile using methods and devices known in the art which prevent the introduction of contaminant therein. As discussed herein, "conditions which may not be sterile" include clinical settings (e.g. doctors' offices, operating rooms, ambulances, etc.) and non-clinical settings (e.g. non-medical buildings, places of residence, the outside environment, etc.). Such "conditions which may not be sterile" may, in fact, be sterile or aseptic, but the sterile or aseptic state of the conditions under which the fill system is being assembled is not known by the person(s) assembling the fill system.

For example, a starting container (e.g. 100, FIG. 2A or 2B), a system of fluid lines (e.g. 200, FIG. 3), and a plurality of containers (e.g. 300, FIG. 4) are each assembled in a sterile environment which may be the same or different. The starting container and the plurality of containers are each assembled to have at least one fluid line connected thereto. Then the free ends (i.e. ends that are not attached to another component) of the fluid lines of the starting container, the system of fluid lines and the plurality of containers are hermetically sealed to form three separate sterile and closed systems. A commercially available sealing device such as Hematron III device (Fenwal, Inc., Lake Zurich, Ill.) may be used to hermetically seal the ends of the fluid lines. For example, the free ends of the fluid lines of the starting container, e.g. fluid line 105 and a fluid line attached to the fluid line connector 104a, are hermetically sealed in the sterile environment to form a first sterile and closed system. Similarly, the free ends of the fluid lines of the system of fluid lines, e.g. fluid line 201 and 203, are hermetically sealed in the sterile environment to form a second sterile and closed system. Likewise, the free end of each fluid line attached to each container of the plurality of containers, e.g. fluid lines connected to fluid line connector 302, are hermetically sealed in the sterile environment to form a third sterile and closed system.

Then the three sterile and closed systems are joined to form one sterile and closed system such that the starting container, the system of fluid lines, and the plurality of containers are in fluidic communication by using methods and devices known in the art that connect the free ends of the fluid lines to each other without introducing significant amounts of biological contaminants. An example of such a suitable commercially available device is the TSCD® Sterile Tubing Welder system available from Terumo (Eschborn, Germany). When such a device is used, the sterile and closed systems need not be connected together in a sterile environment. Nevertheless, it is noted that where all the components of the starting container, the system of fluid lines and the plurality of containers are assembled in a sterile environment and the starting container and the plurality of containers are connected to the system of fluid lines in the sterile environment, the free ends of the fluid lines need not be hermetically sealed and then joined to each other using methods and devices known in the art that connect the free ends of the fluid lines to each other without introducing significant amounts of biological contaminants.

Once the starting container, the system of fluid lines and the plurality of containers are joined and form one closed system, the closed system, in particular the plurality of fluid lines connected to the plurality of containers are connected to a pump head (e.g. 401, FIG. 5) of a peristaltic pump (e.g. 400, FIG. 5) to form a fill system in accordance with the present invention. In some preferred embodiments, the connection of the pump head to the plurality of the fluid lines does not breach the closed system.

In some embodiments, the starting material may be already present in the starting container prior to connecting the starting container to other components of the fill system. In some embodiments, the starting material may be added to the starting container after assembly of a closed system (e.g. connection to the system of fluid lines) or assembly of the fill system. In some embodiments, an additive, such as a cyroprotectant (e.g. DMSO), may be provided in a container that is separate from the starting container, but is capable of being in fluidic communication with the starting container. For example, fluid flow between the starting container and the container having the additive may be restricted by a fluid flow regulator. Then when the additive is to be added to the starting material, the fluid flow regulator is disengaged and the additive is caused to flow into the starting chamber and then mixed with the starting material in the starting chamber.

Exemplary Operation

Once the starting material is present in the starting container and the plurality of fluid lines connected to the plurality of containers are connected to a pump head, the peristaltic pump may be activated in the forward direction such that the starting material (or the suspension) begins to flow through the system of fluid lines towards the plurality of containers. An additive may be added to the starting container or added to the closed system via one or more inlet ports in the system of fluid lines or one or more inlet ports of the plurality of containers. In some preferred embodiments, the additive is added to the starting container and mixed with the starting material therein to give the suspension to be added to the plurality of containers. In some preferred embodiments, equal amounts of additive are added to each of the containers of the plurality of containers, before, during, and/or after the starting material is provided in the plurality of containers, wherein the starting material and additive are mixed to give the suspension.

When fluid flow in a fill system according to the present invention is desired, the component from which the fluid is to flow is preferably placed higher than the component to which fluid is to flow in order to minimize gravitational forces acting against the peristaltic pump. For example, when fluid is to flow from the starting container to the plurality of containers, the starting container is preferably placed at an elevation that is higher than the plurality of containers. In some embodiments, the portion of the system of fluid lines in which fluid flows toward the pump head is elevated above the portion of the system of fluid lines in which fluid flows away from the pump head. When the direction of fluid flow is to be reversed, the relative elevations of the components of the fill system may be changed accordingly such that the component from which the fluid is to flow is preferably placed higher than the component to which fluid is to flow in order to minimize gravitational forces acting against the peristaltic pump. When fluid flow is not desired (e.g. removal of air from the plurality of containers), the components of the fill system may be placed at the same elevation, or the component(s) comprising the fluid may be placed at a lower elevation than the other components. In some embodiments, fluid flow regulators may be engaged in order to prevent fluid flow from one portion to another portion of the fill system. In some embodiments, all the fluid flow pathways from the starting container to each container of the plurality of containers are of the same shape and size, i.e. volume, such that the rates of fluid flow through the fluid flow pathways are substantially similar or the same, and thereby result in substantially similar or the same concentrations and volumes of the suspension being delivered to the plurality of containers.

As the action of the peristaltic pump may cause a vacuum effect in a portion of a fill system according to the present invention and thereby cause the walls of the portion of the fill system to collapse and form a temporary seal which prevents fluid flow, one or more additional containers containing a fluid, e.g. a syringe containing air, may be placed in fluidic communication along one or more fluid flow pathways of the closed system. Then when the walls of a portion of the fill system collapse from the vacuum effect of the peristaltic pump, fluid from the additional container (e.g. air from a syringe) upstream of the collapsed walls may be injected into fluid flow pathway to relieve the vacuum effect and break the temporary seal and thereby allow fluid flow through. In some embodiments the fluid of the additional container is air. In some embodiments, the fluid in the additional container is an inert substance, i.e. a substance that does not react with or dissolve in the starting material or the suspension.

A fluid such as air present in the starting container, the system of fluid lines, and/or the plurality of containers may be removed from these locations using one or more empty containers, e.g. an empty syringe, in fluidic communication with the component from which the fluid is to be removed. The empty container may be the same or different from the container which previously contained the fluid for breaking the temporary seal caused by the vacuum effect of the peristaltic pump as described above. For example, air in one or more of the plurality of containers may be removed therefrom by orienting the container such that a port of the container is located at the top portion where the air is located, passing the air from the container through the ports into a fluid line connected thereto, and then removing the air from the fluid line by using a syringe attached thereto to draw out the air. In some embodiments, the empty container, e.g. syringe, may be connected, directly or indirectly, to the component, e.g. container, from which the fluid is to be removed. In some embodiments, after the fluid is removed, the port of the container is closed or sealed such that the fluid may not flow back into the container. In some embodiments, the empty container, e.g. syringe, is connected to a fluid line or a container (from which the fluid is to be removed) by a fluid line connector which is also a fluid flow regulator and after the fluid is removed, the fluid flow regulator is engaged to prevent the fluid from flowing back into the container. In some embodiments, air from the plurality of containers is evacuated from the plurality of containers by using the peristaltic pump such that the air is drawn from the plurality of containers into the system of fluid lines towards the pump head. In some embodiments, air in the system of fluid lines and/or the plurality of containers is flowed into the starting container. In some embodiments, air may be removed from the system of fluid lines and/or the plurality of containers at periodic intervals. For example, after some of the suspension has been delivered to the plurality of containers, some or all of the air in the plurality of containers may be removed as described above, e.g. reversing the action of the peristaltic pump, then after more suspension is delivered to the plurality of containers, reversing the action of the peristaltic pump again to remove some or all of the air in the plurality of containers, and repeating as necessary until the plurality of containers are filled with the desired volume of the suspension (and the desired amount of air, if any). In some embodiments, an aliquot of a material, e.g. the suspension, starting material, or additive, in the closed system may be removed for testing by using an empty container as described above.

In some embodiments, a second starting container and a second peristaltic pump connected to a second system of fluid lines which are connected to the plurality of containers may be used to deliver a second starting material, which may be an additive or a second suspension (which may or may not be the same as the first suspension) to the plurality of containers. The second starting material may be delivered to the plurality of containers before, during, and/or after delivery of the first starting material or first suspension. The plurality of containers may be agitated during and/or after delivery of the first and second starting materials/suspension in order to ensure thorough mixing therein.

Operation of the devices and fill systems according to the present invention may be manual or automated. In some embodiments, one or more sensors that detect the presence or absence of a fluid may be placed at one or more locations, e.g. in one or more fluid lines of the plurality of fluid lines connected to the plurality of containers, in one or more containers (starting container and plurality of containers), in the pump head of the peristaltic pump, etc. The fluid that is detected by the sensors may be a liquid such as the starting material and/or suspension itself, a gas such as air, or both. In some embodiments, sensors which are capable of detecting and distinguishing between two or more substances are employed. When a sensor detects the presence of a substance, e.g. air, at an undesired location within the fill system, a notification, such as a beep, light or readout on a user interface screen, of such is provided by the fill system. An operator may then manually remove the substance from the undesired location as described above. Alternatively, the fill system may be attached to a computer system and controller which automatically, according to a given computer program, operates the peristaltic pump, orientates and/or agitates the starting container, system of fluid lines and/or plurality of containers based on information received from the sensors. The controller may be the same or different from the control system of the peristaltic pump.

Once the plurality of containers are filled as desired, each container of the plurality may be sealed, preferably hermetically sealed, detached from the system of fluid lines and stored until further use. In some embodiments, the containers are stored in their holder(s) used while filling the containers with the suspension. In some embodiments, the holders contain individual compartments in which each container is held. In some embodiments, the individual compartments are removably attached to each other such that an individual compartment containing a container may be separated therefrom. The peristaltic pump may then be removed, sterilized and reused. In some embodiments, the starting container and the system of fluid lines are used only once.

In some embodiments, the entire fill system is operated at a preset temperature, e.g. in a room at 4° C. or another desired temperature. In some embodiments, one or more components of the fill system may be brought to a desired temperature, e.g. pre-chilled to 4° C. prior to operation. In some embodiments, the starting material and/or the additive may be brought to a desired temperature prior to operating the fill system. In some embodiments, one or more holders containing the starting container and/or the plurality of containers may be brought to a desired temperature prior to operation of the fill system. In some embodiments, one or more holders containing the starting container and/or the plurality of containers may be maintained at a desired temperature before, during and/or after operation of the fill system. In some embodiments, the holders may contain cooling and/or heating elements incorporated within the walls of the holders. In embodiments where multiple holders are employed, the temperatures of the holders may be the same or different. Additionally, the temperature of a given holder may be modified before, during and/or after operation of the fill system.

Exemplary System and Operation for Providing Multiple Cell Suspensions for Cyropreservation Prior to the present invention, the use of a plurality of fluid lines to gravity fill a plurality of containers of a cell suspension generally took almost about 30 minutes after the starting material containing the cells was mixed with a cyropreservative in the starting container. With such methods and devices, ensuring that each container of the plurality of containers contained uniform volumes and concentrations of the cell suspension was challenging and generally not feasible under conditions where the cells are not to be contacted with the cyropreservative for periods of about 30 minutes or longer.

In some preferred embodiments, a fill system according to the present invention is used to provide multiple cell suspensions for cryopreservation. In some embodiments, the cells of the cell suspensions are liver cells. In some embodiments, the liver cells are from one or more donors and the cell suspensions are to be transplanted into one or more subjects being treated.

In some embodiments, the starting material containing the liver cells are mixed with a cyroprotectant, e.g. DMSO, in the starting container, before or after, preferably after (and just prior to operation) assembly of the fill system according to the present invention. The cyroprotectant is provided in the form of a composition which comprises Human Serum Albumin (HSA), Hydroxyethyl Starch (HES), and DMSO. In some embodiments, the composition and the starting material are mixed in a 1:1 volume ratio.

Once the cell suspension (i.e. mixture of the starting material and the cyroprotectant) is to be distributed to the plurality of containers, any fluid flow regulators are opened and the peristaltic pump is activated to move fluid from the starting container towards the plurality of containers. After some or all of the cell suspension is delivered to the plurality of containers, the operation of the peristaltic pump is reversed such that air in the plurality of containers and/or the plurality of fluid lines may be removed therefrom as described above. Once the desired volume of the cell suspension is delivered to the plurality of containers and the desired amount of air has been removed therefrom, the containers may be sealed, preferably hermetically sealed, and detached from the plurality of fluid lines.

In some embodiments, the cyroprotectant may be added to the plurality of containers after the starting material has been added thereto, thereby eliminating the need to mix the starting material and the cyroprotectant before operation of the peristaltic pump and reducing the amount of time the cells are exposed to the cyroprotectant at temperatures over 4° C. In some embodiments, the starting material, the cyroprotectant (or composition containing the cyroprotectant), and/or one or more components of the fill system (e.g. the starting container, the plurality of containers, etc.) is chilled to a temperature ranging from about 2-8° C. prior to operating the fill system. Alternatively, operation of the fill system is conducted in a cold room having a temperature ranging from about 2-8° C.

According to the present invention, the systems, devices and methods of the present invention enable the concurrent distribution of uniform concentrations and volumes (e.g. 60 mL in each container) of cell suspension into multiple containers (e.g. 2 or more, preferably about 4-16) in about 1-23 minutes, preferably about 1-18 minutes, more preferably about 1-13 minutes, and most preferably about 8 minutes or less after the addition of the cryoprotectant to the cell suspension.

To the extent necessary to understand or complete the disclosure of the present invention, all publications, patents and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A closed and sterile system comprising
    a starting container;
    a system of fluid lines having a plurality of fluid lines;
    a plurality of containers;
    a fluid flow regulator
    at least one multi-connector
    a connecting fluid line which connects the starting container with the system of fluid lines; and
    a syringe connected to the connecting fluid line, wherein the connector for connecting the syringe to the fluid line allows for pushing fluid or gas into and removing fluid or gas out of the connecting fluid line through the syringe connector;
    wherein each container of the plurality of containers is connected to a fluid line of the plurality of fluid lines so as to form a closed system in which a fluid may flow from the starting container through the system of fluid lines to the plurality of containers; and
    wherein the plurality of containers are each independently removably attached to each other via the system fluid lines; and
    wherein the plurality of fluid lines are arranged in uniform and parallel fashion and are each engaged with one channel of the multichannel peristaltic pump; and
    wherein the plurality of fluid lines have fittings which can be used to secure the plurality of fluid lines in a pump head of a multichannel peristaltic pump;
    wherein the at least one multi-connector and fluid flow regulator are upstream of the multichannel peristaltic pump; and
    wherein the uniform and parallel arrangement of the fluid lines and placement of the at least one multi-connector and a syringe upstream of the multichannel peristaltic pump of the closed and sterile system divides and dispenses uniform concentrations and amounts of a suspension into the plurality of containers from the starting container when the multichannel peristaltic pump is operated in the forward direction.

2. A method of preparing a plurality of containers having a suspension of a solid wherein the concentrations of the solid in the plurality of containers are substantially similar or the same and the volumes of the suspension in the plurality of containers are substantially similar or the same, which comprises
    obtaining a closed and sterile system according to claim 1, providing a starting material having the solid therein in the starting container, engaging the plurality of fluid lines in a pump head of a peristaltic pump, operating the peristaltic pump in a forward direction so as to cause the starting material to flow from the starting container to the plurality of containers, and optionally adding an additive to the starting material.

3. The method of claim 2, and further comprising removing an excess fluid from the plurality of containers by operating the peristaltic pump in a reverse direction so as to cause the excess fluid to flow from the plurality of containers towards the starting container.

4. The method of claim 2, and further comprising sealing off and detaching the plurality of containers.

5. The closed and sterile system of claim 1 further comprising a plurality of fluid flow regulators.

6. The closed and sterile system of claim of claim 5, wherein at least one fluid flow regulator is downstream of the multichannel peristaltic pump.

* * * * *